United States Patent [19]
Kiemle

[11] 4,008,967
[45] Feb. 22, 1977

[54] DEVICE FOR TESTING MASKS FOR SEMICONDUCTOR COMPONENTS

[75] Inventor: Horst Kiemle, Neuried, Germany

[73] Assignee: Siemens Aktiengesellschaft, Berlin & Munich, Germany

[22] Filed: Aug. 19, 1975

[21] Appl. No.: 605,913

[30] Foreign Application Priority Data
Aug. 29, 1974 Germany .................... 2441336

[52] U.S. Cl. ................ 356/239; 350/285; 356/200
[51] Int. Cl.² ............... G01N 21/32; G02B 27/17
[58] Field of Search ........... 356/71, 158, 160, 167, 356/200, 238–239; 250/234–236, 572; 350/285

[56] References Cited
UNITED STATES PATENTS

| | | | |
|---|---|---|---|
| 3,405,614 | 10/1968 | Lin et al. | 350/3.5 |
| 3,508,808 | 4/1970 | Schmidt | 356/71 |
| 3,776,616 | 12/1973 | Douklias | 356/71 |
| 3,802,762 | 4/1974 | Kiemle | 356/71 |
| 3,814,943 | 6/1974 | Baker et al. | 250/572 |

*Primary Examiner*—John K. Corbin
*Assistant Examiner*—Wm. H. Punter
*Attorney, Agent, or Firm*—Hill, Gross, Simpson, Van Santen, Steadman, Chiara & Simpson

[57] ABSTRACT

A device for testing masks, such as used in producing semiconductor components characterized by a source projecting a beam of coherent light at the mask, a multiple optic means which is either a lens raster or an objective lens arranged with a multiple hologram disposed in the path of the beam of light for converting the beam into a plurality of individual beams and focusing each of the individual beams on discrete points on the mask and a detector for detecting any light passed by the mask. Preferably, the device includes means for pivoting the beam from the source about one or two axes lying in a plane of the multiple optic means so that all of the individual beams are moved to scan in at least one direction.

8 Claims, 2 Drawing Figures

DEVICE FOR TESTING MASKS FOR SEMICONDUCTOR COMPONENTS

BACKGROUND OF THE INVENTION

The present invention is directed to a device for automatically testing masks such as masks utilized in producing semiconductors which device utilizes a beam of coherent light and a detector arrangement.

The yield in the production of semiconductor components is often determined by the mask, which is used in exposing the light-sensitive layers, being free from faults. In the course of use, a mask frequently suffers damages such as indents, holes, scratches or becomes dirty due to adhering foreign bodies or particles. These faults or particles subsequently lead to the breakdown in the pattern being exposed on the component and render the component unusable for its intended purpose. In order to recognize in time that the mask has become unserviceable due to wear or from becoming dirty, and to be able to replace the mask, a mask testing arrangement which operates as rapidly as possible and as automatically as possible is desired.

Normally, masks are visually inspected under a microscope. However, on account of the extremely fine structure of the mask, a visual inspection is a time consuming operation. Thus, it was only possible to spot check portions of the mask and therefore only obtain statistical information concerning the state or condition of the mask.

It has been suggested to investigate the mask with the aid of an electro-optical deflected light beam which is focused with the aid of an objective lens onto the mask surface which is to be checked. The light which passes through the mask is intercepted by a photoelectric detector and is electrically analyzed. The light spot must execute a row by row scanning movement on the mask surface which scanning movement is achieved by the beam only partially illuminating the diameter of the objective lens and by the beam being conducted across the entire surface of the lens in a corresponding scanning motion.

This type of arrangement will only insufficiently fulfull the aims for testing the mask because of the following two reasons. In order to obtain the requisite scanning motion, the focusing lenses are only partially illuminated. Such illumination produces a scanning point which has a substantially poorer degree of resolution than the resolution which would be achieved by completely or fully illuminating the objective lens. Another difficulty with this proposed type of arrangement or device is that even a sophisticated objective lens does not permit the handling of an image field of the size of the entire semiconductor waffer with a resolution of the finest structures of the mask. Thus, this proposed device causes one to dispense with the discovery of the finer faults which may be present and on the other hand requires scanning times in the region or range of a number of minutes. Thus, only a relatively coarse testing of the mask can be carried out with this suggested device.

SUMMARY OF THE INVENTION

The present invention is directed to providing a device for testing masks particularly those utilized in the production of semiconductor components which device operates automatically and rapidly and thus can be used for routine tests of all masks.

To accomplish these aims, the device includes means supporting a mask to be tested, a source projecting a beam of coherent light at the mask, multiple optic means disposed in the path of the beam of the coherent light for converting the beam into a plurality of individual beams and for focusing the individual beams onto the mask, and means for detecting light from each of the individual beams which light passes through the mask. Preferably, the means for detecting includes a photoelectric detector for each one of the plurality of individual beams. The multiple optic means may be either a lens raster, or an objective lens arrangement and a multiple hologram. Preferably, the device includes means for pivoting the light beam from the light source about at least one axis which is in a plane of the multiple optic means so that all of the individual beams are moved together to scan the mask in at least one direction.

Figure 1:
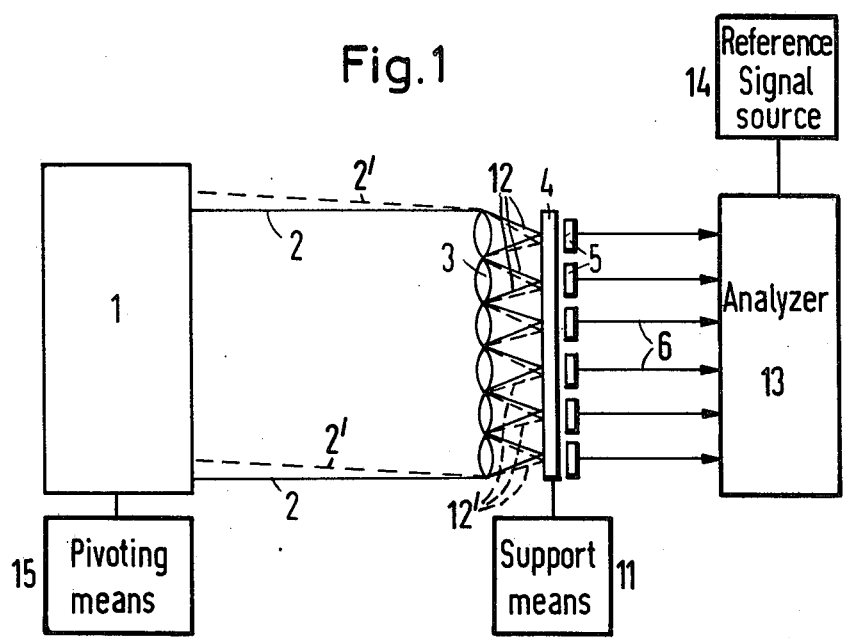
FIG. 1 is a schematic presentation of an embodiment and device according to the present invention.

DESCRIPTION OF THE PREFERRED EMBODIMENTS the principles of the present invention are particularly useful when incorporated in an exemplary embodiment illustrated in FIG. 1. In this embodiment, a source 1, such as a laser, produces a beam 2 of coherent light and projects the beam 2 through a multiple optic means 3 onto a mask 4, which is supported by means 11 for supporting the mask. The multiple optic means 3 is illustrated as consisting of a lens raster commonly known as a "fly-eye-lens" which is composed of a plurality of lens elements arranged in rows and columns. The lens raster converts the beam 2 into a plurality of individual beams 12 and focuses each one of the individual beams 12 to a separate point on the mask 4, which points would be arranged in rows and columns.

To detect the light which is passing through the mask, a detecting means composed of a plurality of photoelectric detectors 5 are disposed on the rear or opposite side of the mask with a separate detector 5 arranged to receive light from each of the beams 12. Each of the detectors, which convert the amount of light detected into an electrical signal, is provided with an output lead 6 which extends to a signal analyzer 13, which receives a reference signal from a reference signal source 14 and produces an output signal or indication if a fault occurs.

The beam 2 of coherent light has a cross section to fully illuminate all of the lens elements of the lens raster. To obtain a scanning motion for each one of the individual beams 12, pivoting means 15 are provided for pivoting the beam 2 about one or more axes disposed in the plane of the lens raster 3. This pivoting produces a simultaneous pivoting of all of the individual beams 12 to produce a scanning of the surface of the mask 4. The pivoting of the beam 2 can be accomplished by the pivoting means 15 either shifting the source 1 or imposing a deflection of the beam 2. The broken lines 2' illustrate a position of the beam 2 in a pivoted position and produces a pivoting of the individual beams 12 to a position illustrated by the broken lines 12'. It should be noted that the mask 4 will have a plurality of fine patterns which are arranged in columns and rows and that the lens raster has a lens element for each of the patterns. Thus, one individual beam 12 is present for scanning each of the individual patterns on the mask.

Figure 2:
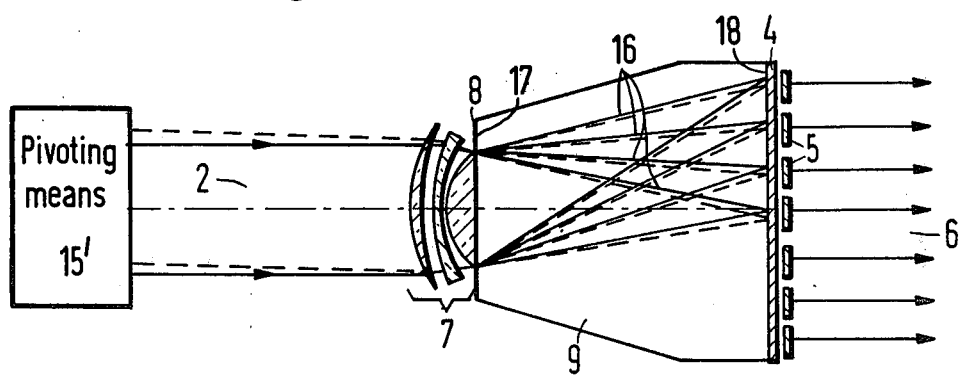
FIG. 2 is a schematic presentation with portions in cross section of a second embodiment of the device of the present invention.

Another embodiment is illustrted in FIG. 2. In the embodiment of FIG. 2, a beam 2, which is coming from a means 15' for pivoting the beam 2 after it leaves the laser, is directed at a multiple optic means including a high grade objective arrangement 7 and a multiple hologram 8. The high grade objective lens arrangement 7 and the multiple hologram 8 coact to form a plurality of individual beams 16 which are focused at different points or spots on the mask 4. As in the previous embodiment, the detecting means including a plurality of photo detectors 5, which are arranged with a photo detector for each one of the individual beams 16. Each detector 5 has an output lead 6.

The use of the high grade objective 7 and the multiple hologram 8 makes it more easy to produce a plurality of highly convergent scanning beams 16 which are required for a high degree of resolution. A further improvement in the resolution is achieved if the space between the multiple optic means and the mask 4 is filled with immersion means having an index of refraction which is as high as possible. The light wavelength, which is as known to decisively co-determine resolution, is thus reduced by a factor of the index of refraction. In the embodiment illustrated in FIG. 2, a glass body 9 consisting of glass with a high index of refraction is provided as the immersion means. The body 9 is illustrated as having a pair of opposed flat surfaces 17 and 18 with one surface 17 supporting the multiple hologram 8 and the other surface 18 supporting the mask 4 and acting as a supporting means. The multiple hologram 8 is preferably formed in a layer which was deposited on the surface 17.

The electrical signals emitted by the detectors 5 can be automatically analyzed. In one way of analyzing, it is expendient to form the difference of each of the individual signals with a referecne signal and to identify deviations which exceed a specific value as mask faults. The reference signal can be obtained by an optical comparator channel which is fundamentally of the same construction as the mask testing arragnement and which signal is determined by the light passed by a fault-free individual image of the mask. Thus, a scanning of each of the individual masks by the plurality of beams 12 or 16 will determine the amount of light transmitted by the mask at each scanning point which is compared with a reference signal. A defect such as a scratch or dirt will effect the light transmitted by a mask at a given point, and when the amount of light exceeds or is less than a predetermined amount, a fault of the mask will be indicated. In this testing arrangement, synchronization of the scanning of the beams 12 or 16 with the reference signal must be accomplished and this may be done by conventional means.

In another simpler arrangement of analyzing the signals from the detectors 5 is to electrically add all of the signals from the detectors 5 and obtain a mean value signal. The output signal of each detector is conducted to a differential amplifier whose other input posses a reference voltage. The outputs of the differential amplifier is connected to an electronic analyzing unit. This analyzing principle is based on the experience that wear phenomena are statistically distributed over the mask surface and the addition of the detector signal comes very close to the signal of the fault-free mask. Thus, when a fault is present in the mask, the mean value signal will differ from the reference signal to provide an indication of the presence of the faults. However, faults in the mask image, which are due to errors in drawing or constructing of the mask, may not be discovered by this means since the total light passed by the mask may be the same although the mask patterns are different.

The mask testing device of the present invention when compared to known testing processes enables both a considerable increase in the resolution such as down to 1 $\mu$m. Due to simultaneously testing of all of the individual images or patterns of the mask, the device of the present invention provides a substantial shortening in the time required for complete testing of the mask.

Although various minor modifications may be suggested by those versed in the art, it should be understood that I wish to employ within the scope of the patent granted hereon, all such modifications as reasonably and properly come within the scope of my contribution to the art.

I claim:

1. A device for automatically testing a mask and particularly masks used in producing semiconductor components comprising means supporting a mask to be tested, a source projecting a beam of coherent light at said mask, multiple optic means disposed in a path of the beam of coherent light for converting the beam into a plurality of individual beams and focusing the individual beams onto the mask, means for detecting light from each of the invdividual beams passing through the mask, and means for pivoting the light beam from the source about at least one axis lying in a plane of the multiple optic means so that all of the individual beams are moved together to scan the mask in at least one direction.

2. A device according to claim 1, wherein said multiple optic means is a lens raster disposed in said plane.

3. A device according to claim 1, wherein said multiple optic means includes an objective lens and a multiple hologram.

4. A device according to claim 3, which includes a submersion body disposed between said multiple hologram and mask.

5. In a device for automatically testing masks used in producing semiconductor components, said device comprising a source projecting a beam of coherent light at the mask and means for detecting the light which passes through the mask, the improvement comprising multiple optic means disposed in the path of the beam of light for converting the beam into a plurality of individual beams and focusing each of the individual beams onto the mask, said multiple optic means having a plane and means for pivoting the beam of coherent light about at least one axis lying in the plane so that all of the individual beams move together to scan in at least one direction.

6. In a device according to claim 5, wherein the detecting means includes a pluarlity of photoelectric detectors with one photoelectric detector associated with each one of the individual beams.

7. In a device according to claim 5, wherein the multiple optic means comprises a lens raster disposed in said plane.

8. In a device according to claim 5, wherein the optic means includes an objective lens arrangement and a multiple hologram.

* * * * *